United States Patent [19]

Veazey et al.

[11] Patent Number: 4,694,047

[45] Date of Patent: Sep. 15, 1987

[54] HALOGENATED POLY(ALLOOCIMENE)

[75] Inventors: Richard L. Veazey, East Windsor, N.J.; Kathryn S. Hayes, Norristown, Pa.

[73] Assignee: Union Camp Corporation, Wayne, N.J.

[21] Appl. No.: 927,921

[22] Filed: Nov. 6, 1986

[51] Int. Cl.[4] .................................................. C08F 8/22
[52] U.S. Cl. .............................. 525/332.3; 525/331.9; 525/356; 526/290; 526/340.3
[58] Field of Search .................... 525/331.9, 332.3; 526/290, 340.3

[56] References Cited

U.S. PATENT DOCUMENTS

| | | | |
|---|---|---|---|
| 2,406,575 | 8/1946 | Young et al. ..................... | 525/331.9 |
| 3,278,641 | 10/1966 | Bell, Jr. ............................ | 526/340.3 |
| 3,373,149 | 3/1968 | Doyle, Jr. ......................... | 528/393 |
| 3,715,341 | 2/1973 | Velzmann ......................... | 528/374 |
| 3,929,850 | 12/1975 | Streck et al. ..................... | 526/279 |
| 3,939,131 | 2/1976 | Morikawa et al. ............... | 526/308 |
| 4,169,116 | 9/1979 | Trotter et al. .................... | 525/210 |
| 4,229,549 | 10/1980 | Ugemi et al. ..................... | 525/308 |
| 4,282,337 | 8/1981 | Roggero et al. .................. | 525/285 |
| 4,388,359 | 10/1981 | Trotter et al. .................... | 525/232 |
| 4,524,187 | 6/1985 | Greco et al. ...................... | 525/342 |

*Primary Examiner*—Joseph L. Schofer
*Assistant Examiner*—Bernard Lipman
*Attorney, Agent, or Firm*—Edward J. Sites

[57] ABSTRACT

Halogenated poly(alloocimene) is described. The polymer is useful in coatings as barrier resin, slow release material for pesticides and the like.

14 Claims, 1 Drawing Figure

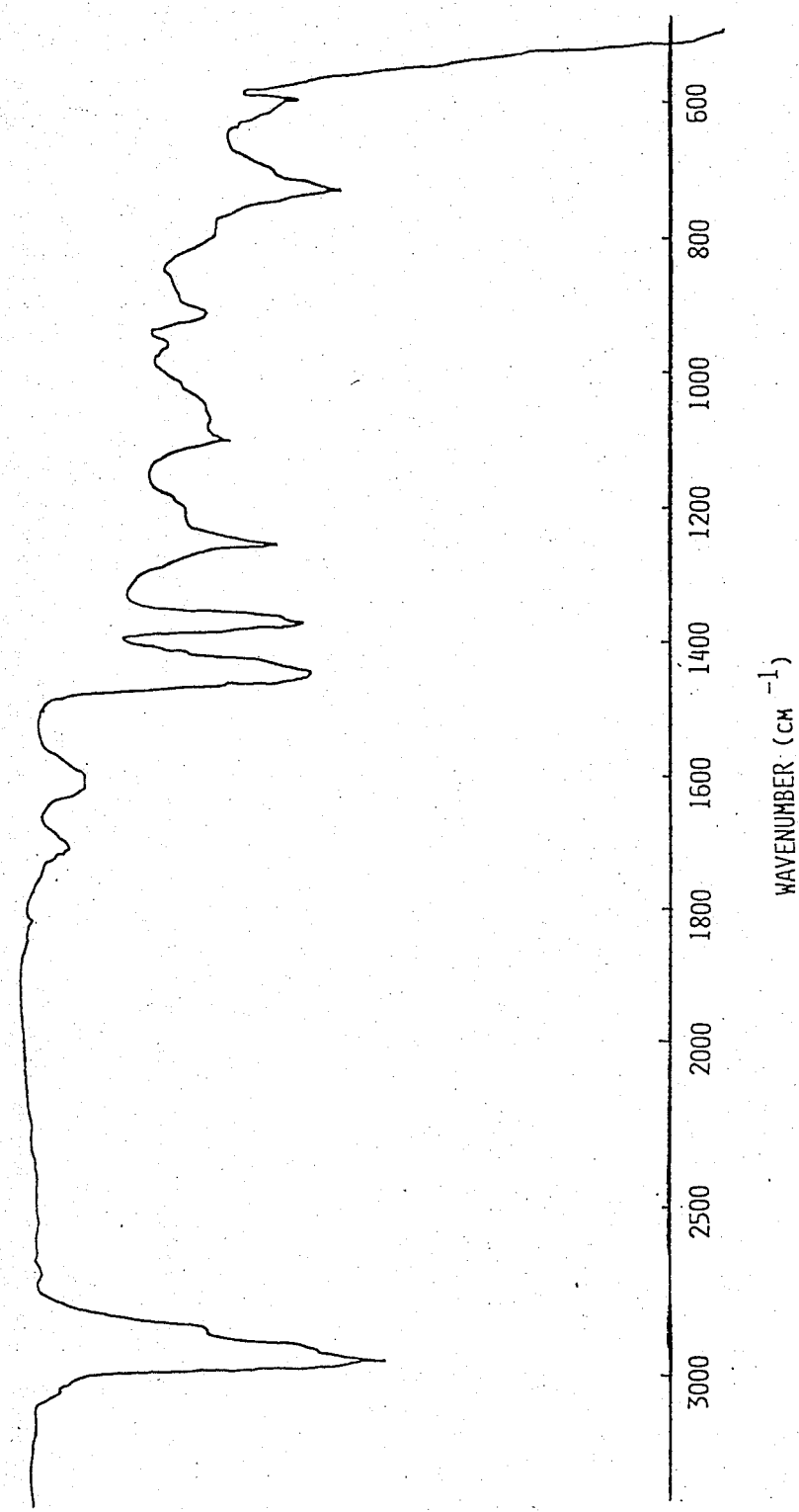

HALOGENATED POLY(ALLOOCIMENE)

This invention is related to halogenated poly(alloocimene) polymers and the method for the preparation thereof.

BACKGROUND OF THE INVENTION

Halogenation of polymers and terpene resins has been known in the prior art for some time. For example, David W. Young and Harris D. Hineline in U.S. Pat. No. 2,406,575 disclosed treatment of various polymers with chlorinating agents such as $AlCl_3$, $SnCl_4$, and $PCl_5$ gave rise to chlorinated cyclized polymers useful as lubricants. The $PCl_5$ treatment of a cyclized alloocimene polymer was claimed to give chlorination. Although some chlorination of olefins can occur with $PCl_5$, it is mainly utilized for other purposes such as the formation of acid chlorides or as a Lewis acid as reported in *Reagents for Organic Synthesis* by L. F. Fieser and M. Fieser, John Wiley and Sons, New York, 1967, pp 866-870.

Typically when polymers are chlorinated, chlorine gas either used alone or in solution is employed. For example, Paul T. Parker and Fred J. Buchmann in U.S. Pat. No. 3,397,174 disclose the chlorination of a poly(isobutylene) copolymer by adding chlorine gas to the polymer at 30° C. in a Pfaudler reactor.

A novel class of highly unsaturated poly(alloocimene) is disclosed in copending application Ser. No. 919,884 filed Oct. 16, 1986.

SUMMARY OF THE INVENTION

A novel class of halogenated 2,3- and 4,7-poly(alloocimene) polymers is disclosed. The halogenated poly(alloocimene) polymers of the invention are useful in coatings, as barrier resins, as slow release materials, as pesticides, and the like.

DESCRIPTION OF THE DRAWINGS

The drawing is the infrared spectrum of chlorinated poly(alloocimere).

DETAILED DESCRIPTION OF THE INVENTION

The terms "halogenated" and "halogenating" as used herein refer to the halogens, which are embracive of fluorine, chlorine, bromine, and iodine.

The poly(alloocimene) employed to prepare the polymers of the invention is advantageously the homopolymer of alloocimene having a weight average molecular weight of from about 500 to 100,000 and which contains repeating or recurring chain moieties of the formula:

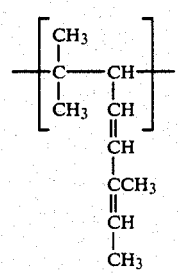

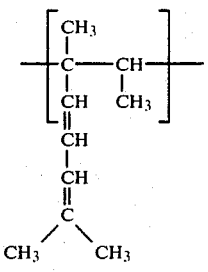

and

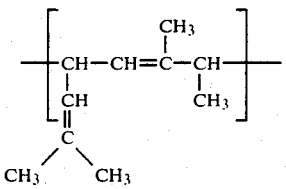

These poly(alloocimene) polymers comprise mixtures of a majority of chain moieties of formulae I and II as a group and a minority of chain moiety of formula III. The term 2,3- and 6,7- poly(alloocimene) as used herein refers to the polymer consisting of greater than 50 weight percent of 2,3-poly(alloocimene), (I), and 6,7-poly(alloocimene), (II), and less than 50 weight percent of 4,7-poly(alloocimene), (III) of polymer chain moieties.

The 2,3- and 6,7-poly(alloocimene) may be prepared in the following manner. Substantially anhydrous alloocimene is added slowly to catalyst system comprised of an active metal component dispersed in a substantially anhydrous ether component under an inert gas atmosphere. Controlled reaction by slow alloocimene addition is necessary because the polymerization is highly exothermic. It is preferred that the alloocimene feed be essentially free of peroxides, water, and alcohols. The metal component may be any alkali metal or calcium. The metal component should be substantially free of surface oxides or other contaminants and present at a concentration of less than about 10 mole percent of the alloocimene. The active metal component may be present as spheres, wire, foil, or a finely divided dispersion and may be in the pure state, as a mixture or an alloy, or as a solution with aromatic hydrocarbons, such as naphthalene, 2-methylnaphthalene, and the like.

The ether components used in the catalyst systems are the aliphatic and cycloaliphatic ethers. The ether component is preferably present in an amount greater than about 5 weight percent of the alloocimene. The most preferred ether components are tetrahydrofuran and 1,2-dimethoxyethane. Inert hydrocarbon solvents and diluents may also be present, for example, benzene, toluene, xylene, ethylbenzene, pentane, hexane, cyclohexane, heptane, octane, nonane, limonene, p-cymene, and the like, or mixtures thereof.

The polymerizations are carried out at temperatures of from about −78° C. to about 100° C., with reaction times of from about 10 minutes to about 500 hours. Most preferably the polymerizations are carried out at temperatures of from about −30° C. to about 60° C., with reaction times of from about 1 to about 8 hours.

When the polymerization is complete, addition of a proton source, for example, water, an acid, an alchol, or mixtures thereof, in molar excess of the alkali metal catalysts terminates the reaction and thereby introduces hydrogen atoms at the end of ends of the polymeric chain.

Following the polymerization, the reaction mixture containing the poly(alloocimene) is subjected to distillation to remove the ether component and any unreacted reagent. Care must be taken not to exceed a temperature of about 150° C. in the distillation pot containing the polymer, otherwise excessive thermal degradation of the polymer will occur. The polymer may be discharged while still molten onto a polytetrafluorethylene coated glass fabric or other suitable surface and allowed to cool. The cooled polymer may then be packaged under a nitrogen atmosphere to protect it from oxidation.

A second polymer isolation procedure, although not requisite, may be empolyed especially for higher molecular weight poly(alloocimene). This method involves cautious transfer of the terminally active polymer and diluents into a large excess of a nonsolvent, such as methanol, or the like. The poly(alloocimene) precipitates as a white solid. Collecting, redissolving, and repreciptating the poly(alloocimene) solid several times gives, after finally drying, a poly(alloocimene) free of low molecular weight impurities. The dried, isolated poly(alloocimene) is then packaged and stored in a nitrogen atmosphere.

It is advantageous to add an antioxidant, such as 2,6-di-tert-butyl-4-methylphenol or the like, prior to distillative isolation, or in the final precipitation solvent to protect the poly(alloocimene)from oxidizing.

Alternatively, in cases where the solvent and ether are inert to the halogenating agent, the poly(alloocimene) need not be isolated, but the reaction mixture containing the polymer may be used directly to prepare the halogenated poly(alloocimene) of this invention.

The compounds of this invention are prepared by halogenating 2,3- and 6,7-poly(alloocimene) employing conventional halogenation technique and apparatus; see for example the general method of Parker and Buchmann in the above-cited reference.

More specifically, the polymers of the invention are prepared by dissolving poly(alloocimene) in a suitable solvent that does not react with the halogen, cooling the solution to a temperature within the range of about −50° to about 40° C. preferably below 10° C. and adding the halogen as a gas or in solution to the poly(alloocimene) solution. Halogenation is carried out until there has been a substantial uptake of halogen into the polymer chain. A substantial halogen uptake is typically within the range of from about to 60 weight percent of the total polymer, for most applications, preferably greater than 20 weight percent; most preferably greater than 35 weight percent. After the halogenation is judged complete by the lack of any further halogen uptake, the solution is freed of any excess halogen by purging with an inert gas or working the organic solution with water or chemically neutralizing the excess halogen. The halogenated poly(alloocimene) is isolated by evaporating off the solvent and/or precipitating it in a nonsolvent such as methanol.

The halogenated poly(alloocimene) compounds of the invention can be prepared in a variety of different molecular weights depending on starting molecular weight of the 2,3- and 6,7-poly(alloocimene). Representative molecular weights are in the range of from about 700 to about 100,000.

The compounds of the instant invention are halogenated derivatives of 2,3- and 6,7-poly(alloocimene) which preferably contain about 5–60 weight percent of halogen. The halogenated poly(alloocimene) of this invention can contain a single type of halogen such as chlorine, bromine, iodine or fluorine, or may contain a mixture of halogen groups. Because these materials give off the appropriate hydrohalogenic gas when exposed to moisture, they are useful as slow release materials for various pesticide applications. Other uses of the halogenated poly(alloocimene) of this invention include coating for textiles and paper, a barrier coating and the like.

The following examples describe the manner and the process of making and using the invention and set forth the best mode contemplated by the inventor for carrying out the invention.

Preparation 1

To a clean, oven-dried, three-neck round-bottom flask, equipped with a claisen adapter, thermometer onto which was placed a temperature sensing device, nitrogen inlet, pressure equalizing addition funnel, a reflux condenser into which was inserted an inert gas exit adapter, and a Nicrome wire stirrer, was added sodium shot (46 g) and toluene (75 ml) which had been dried and distilled from calcium hydride. A nitrogen blanket was maintained in the reaction flask at all times. Heat was applied and stirring initiated. The toluene was allowed to gently reflux for 30 minutes, and then it was cooled to less than 50° C. At this point tetrahydrofuran (252 ml) was added. A preweighed sample of the crude alloocimene (1500 ml, 42.2 % pure with the remainder being mostly dipentenes) which had been dried over calcium hydride and distilled, was charged to the addition funnel. The polymerization temperature 25° C. was maintained by applying cooling to the reaction flask with an dry-ice isopropanol bath.

Polymerization was initiated by slowly adding the alloocimene mixture over one hour and forty minutes to the stirred solvent containing sodium metal.

The polymerization was allowed to proceed for an additional 18 hours. The poly(alloocimene) was isolated by transferring about 100 ml portions of the crude product to 50 ml of methanol adding either about 100 ml of toluene or diethyl ether. This solution was thoroughly washed with saturated sodium chloride aqueous solution. The organic solutions were combined and then dried over anhydrous magnesium sulfate and filtered into a round-bottom flask. The solvents were removed at reduced pressures. Any monoterpenes were isolated at approximately 40°–82° C. (at about 10 mm Hg.). The distillation was terminated when the temperature in the pot containing the polymer product reached about 147° C. The polymer was poured while hot into a pan, allowed to cool, then stored under nitrogen. The polymer yield was 482 g, about 92 % of theory. Data for this polymer is reported in Table 1.

Preparation 2

The procedure of Preparation 1 was repeated except 1246 ml of previously dried toluene, 7.6 g (.33 moles) of sodium, 233 ml of 1,2-dimethoxyethane, and 1215 ml of 95% alloocimene (7.245 moles) were utilized at a polymerization temperature of 17°–23° C. The yield was 83.6 weight percent. Other properties of this polymer are reported in Table 1.

TABLE 1

|  | Preparation 1 | Preparation 2 |
|---|---|---|
| GPC |  |  |
| $M_w$ | 5201 | 29207 |
| $M_n$ | 1422 | 9800 |
| $M_w/M_n$ | 3.66 | 2.98 |
| Tg °C. | 20 | 60 |
| UV unit molar absorptivity at 246 mm | 13000 | 14000 |

EXAMPLE 1

Poly(alloocimene), 20 g (0.15 mole), prepared by the procedure of Preparation 1, supra., was dissolved in 150 ml of methylene chloride. The pale, yellow solution was stirred under nitrogen with a mechanical stirrer and cooled to 0° C. Chlorine was bubbled into the flask. Any gas escaping from the reaction flask was bubbled into a beaker of water. The reaction solution turned dark yellow, black, and dark yellow. The reaction was terminated when chlorine was observed bubbling into the water. The flask was flushed with nitrogen, then the solution was washed with water, dried over anhydrous magnesium sulfate, and the solvent was evaporated. The properties of this polymer are reported in Table 2, below.

EXAMPLE 2

To a clean, dry, four-neck 500 ml round bottom flask equipped with a thermometer, thermo-watch, mechanical stirrer, condenser, addition funnel, and nitrogen inlet/outlet are added 20 g of Preparation 1 and 150 ml of methylene chloride. The reaction flask and contents were swept free of any oxygen by purging the flask with dry nitrogen prior to the addition of the Preparation 1 and methylene chloride. Upon the addition of these ingredients the flask contents were blanketed with nitrogen. The reaction temperature was maintained at 10° C. by periodically immersing the reaction flask in an ice-water bath. Bromine 40.6 g (13.1 ml) dissolved in 80 ml of methylene chloride was added at a slow enough rate so that the reaction temperature was maintained at 10° C. The bromine solution addition took 1 hour and 50 minutes. The bromination was allowed to proceed 30 minutes at 10° C. and 16 hours at room temperature (which was about 23° C.).

The brominated polymer was isolated by slowly adding an excess of a 10 weight percent aqueous solution of sodium carbonate to the reaction solution. The reaction flask contents were transferred to a separatory funnel and the aqueous layer separated. The organic layer was washed three times with excess 10% aqueous sodium carbonate. The methylene chloride was removed from the polymer by distillation at reduced pressures. Nitrogen was blown across the polymer to remove any residual solvent. The yield was 28.2 g of a dark black/brown solid. This material is characterized in Table 2.

EXAMPLE 3

Into a 1 liter Erlenmeyer flask containing a magnetic stirrer and about 500 ml of Freon 112 was added about 52 g (0.38 moles) of Preparation 2. This mixture was stirred for two hours. A light amber solution resulted, which was transferred to a polyethylene bottle immersed in an ice-water bath. A Teflon ® dip tube was connected to cylinders of fluorine and nitrogen gases.

After cooling the solution of poly(alloocimene) below 5° C., the fluorination reaction was begun. The fluorine and nitrogen gas flows were adjusted such that a mixture of the two gases would just ignite a cotton swab wetted with acetone. This gas mixture was bubbled into the cooled solution. Immediately HF fumes were observed, and the temperature of the solution begin to rise.

After 5 minutes a gel was observed to be forming in the now reddish-brown solution. The fluorine flow was further reduced with nitrogen. At this time the temperature had risen to 10° C. After 12 minutes the temperature was 13° C. Both HF and $F_2$ were observed in the gas above the reaction. After 32 minutes the solution had gelled sufficiently so that stirring was no longer possible.

The reaction was terminated after 52 minutes by closing the valve to the fluorine gas cylinder. The total amount of fluorine used was about 10 psig. The product appeared to be a black gel dispersed in the dark-colored Freon.

The solution was saturated with nitrogen gas and filtered. The filtrate, freed of the gel, was added to a large excess (about 1 liter) of methanol. The tan solid that precipitated, was collected, dried for 18 hours in air, dissolved in a minimal amount of diethyl ether, and precipitated in methanol a second time. This second precipitate was dried in air. The weight of this material was 5.6 g (10.8 weight percent).

TABLE 2

|  | Example 1 (Cl) | Example 2 (Br) | Example 3 (F) |
|---|---|---|---|
| Elemental Analysis |  |  |  |
| % C | 47.57 | 42.95 | 82.9 |
| % H | 5.62 | 5.37 | 10.5 |
| % halogen | 45.37 | 46.70 | 6.7 |
| Formula derived from analysis | $C_{10}H_{16}Cl_{3.25}$ | $C_{10}H_{16}Br_{1.5}$ | $C_{10}H_{16}F_{.54}$ |
| Capillary Melting Point °C. | 149–151 | >200 | 162–188 |
| Grars Transition Temp (°C.) | not detected | not detected | 15 |
| GPC |  |  |  |
| $M_w$ | 2834 | 5100 | 9031 |
| $M_n$ | 1462 | 1980 | 1655 |
| $M_w/M_n$ | 1.93 | 2.58 | 5.46 |

What is claimed is:

1. Halogenated 2,3- and 6,7-poly(alloocimene).

2. Chlorinated 2,3- and 6,7-poly(alloocimene).

3. A halogenated poly(alloocimene) comprised of a mixture of chain moieties of greater than 50 weight percent halogenated 2,3- and 6,7-poly(alloocimene) and less than 50 weight percent halogenated 4,7-poly(alloocimene).

4. The halogenated poly(alloocimene) according to claim 3 which contain about 5 to about 60 percent by weight of halogen.

5. The halogenated poly(alloocimene) according to claim 4 which contain at least about 20 percent by weight of halogen.

6. The halogenated poly(alloocimene) according to claim 4 which contain at least about 35 percent by weight of halogen.

7. The halogenated poly(alloocimene) according to claim 3 having a molecular weight of from 700 to about 100,000.

8. The halogenated poly(alloocimene) according to claim 3 halogenated with only one type of halogen.

9. The halogenated poly(alloocimene) according to claim 8 wherein the halogen is fluorine.

10. The halogenated poly(alloocimene) according to claim 8 wherein the halogen is chlorine.

11. The halogenated poly(alloocimene) according to claim 8 wherein the halogen is bromine.

12. The halogenated poly(alloocimene) according to claim 8 wherein the halogen is iodine.

13. The halogenated poly(alloocimene) according to claim 3 halogenated with a mixture of at least two different halogens.

14. A chlorinated poly(alloocimene) having the infrared spectrum of the FIGURE in the accompanying drawing.

* * * * *